United States Patent [19]

Reusch et al.

[11] Patent Number: 5,814,821
[45] Date of Patent: Sep. 29, 1998

[54] MOBILE IRRADIATION DEVICE

[75] Inventors: Michael Foster Reusch, Princeton Junction, N.J.; Ian Russell Clarkson, Huntington, N.Y.; Alan Murray Melville Todd, Princeton Junction, N.J.

[73] Assignee: Northrop Grumman Corporation, Los Angeles, Calif.

[21] Appl. No.: 756,427

[22] Filed: Nov. 26, 1996

[51] Int. Cl.$^6$ .................................................. H01J 33/00
[52] U.S. Cl. .......................................................... 250/492.3
[58] Field of Search ........................... 250/492.3, 492.1; 315/5.41, 5.42, 111.61

[56] References Cited

U.S. PATENT DOCUMENTS

| | | | |
|---|---|---|---|
| 4,703,228 | 10/1987 | West | 315/149 |
| 4,800,322 | 1/1989 | Symons | 315/5.39 |
| 5,336,972 | 8/1994 | Sheffield et al. | 315/5.41 |
| 5,357,291 | 10/1994 | Schonberg et al. | 250/492.3 |
| 5,378,898 | 1/1995 | Schonberg et al. | 250/492.3 |
| 5,523,577 | 6/1996 | Schonberg et al. | 250/492.3 |
| 5,541,944 | 7/1996 | Neil | 372/2 |
| 5,635,721 | 6/1997 | Bardi et al. | 250/492.3 |

Primary Examiner—Kiet T. Nguyen
Attorney, Agent, or Firm—Terry J. Anderson; Karl J. Hoch, Jr.

[57] ABSTRACT

A mobile irradiation device for providing either energetic electrons or short wavelength photons, i.e., gamma ray and/or x-rays has a photocathode, a laser for illuminating the photocathode and a radio-frequency electron gun for accelerating electrons emitted from the laser illuminated photocathode. A quadrupole magnet triple facilitates focusing of energetic electrons onto the target or the material to be irradiated.

14 Claims, 3 Drawing Sheets

MOBILE IRRADIATION DEVICE

FIELD OF THE INVENTION

The present invention relates generally to devices for providing energetic electrons and/or short wavelength photons, e.g., x-rays and/or gamma rays. The present invention relates more particularly to a mobile irradiation device for providing energetic electrons and/or short wavelength photons utilizing a photocathode and a laser as an electron source.

BACKGROUND OF THE INVENTION

Devices for facilitating irradiation with energetic electrons, gamma rays, and/or x-rays are well known. As those skilled in the art will appreciate, such radiation sources find application in a variety of different fields. For example, energetic electrons are commonly used to cross-link polymers, sterilize items such as bandages, and facilitate a variety of different chemical processes. Gamma rays and/or x-rays are utilized in a variety of different imaging, inspection, and contraband detection techniques.

Various techniques are utilized according to contemporary methodology for producing such energetic electrons, gamma rays, and/or x-rays. However, all such contemporary methodologies which produce radiation in substantial quantities, i.e., sufficient for industrial processes and/or the inspection of dense materials, utilize large, heavy equipment having substantial power requirements. Thus, such contemporary radiation sources are necessarily confined to operation at a fixed location.

However, many times it is desirable to provide irradiation so as to facilitate industrial processes and/or inspection at a location remote from the fixed location of such contemporary devices. For example, the x-ray inspection of building components, i.e., concrete, rebar, I-beams, etc., which have already been incorporated into a building structure, frequently cannot be performed with low power portable equipment. Also, such building components cannot be removed from the building itself and then transported to the site of a fixed location radiation source so as to facilitate inspection thereof. Thus, in many instances, such highly desirable inspection simply cannot be performed.

In view of the foregoing, it is desirable to provide a mobile irradiation device which is capable of providing energetic electrons, gamma rays, and/or x-rays of sufficient power to facilitate use thereof in various industrial processes and/or inspection methodologies.

SUMMARY OF THE INVENTION

The present invention specifically addresses and alleviates the above-mentioned deficiencies associated with the prior art. More particularly, the present invention comprises a mobile irradiation device for providing either energetic electrons or short wavelength photons, i.e., gamma rays and/or x-rays, for use in industrial processes and/or inspection. According to a presently preferred embodiment of the invention, the mobile irradiation device comprises a photocathode, a laser for illuminating the photocathode, and a radio-frequency electron gun for accelerating electrons emitted from the laser illuminated photocathode.

Optionally, a metal target is positioned in the path of the energetic electrons which have been accelerated by the radio-frequency electron gun, such that the energetic electrons are incident thereupon so as to effect the production of short wavelength photons. Thus, the target produces either gamma rays or x-rays when the accelerated electrons are incident thereupon.

The radio-frequency electron gun is preferably configured to accelerate electrons emitted from the laser illuminated photocathode to an energy of approximately 15 MeV. Focusing elements focus the electrons emitted from the laser illuminated photocathode for transport through the beamline or for impingement upon the target. The focusing elements preferably comprise at least one focusing magnet.

According to the preferred embodiment of the present invention the photocathode, laser, and radio-frequency electron gun, as well as the beamline and spot forming optical elements therefore, are all disposed upon a trailer so as to facilitate transport thereof. A portable power supply is preferably configured to provide approximately 25 kW at approximately 220 V, three phase, for providing power to the mobile irradiation device of the present invention.

The radio-frequency electron gun preferably comprises a power supply comprising a 30 MW, 2,856 MHz Klystron pulsed at 10 Hz and a pulse tank. The laser preferably comprises a 300 mW laser having a wavelength of 1,047 nM and a less than 10 picosecond pulse width, which is capable of being mode locked and of being fired with a frequency of 142.8 MHz.

According to the preferred embodiment of the present invention two frequency doublers double the frequency of the first beam output by the laser to produce a second beam having a wavelength of approximately 262 $\mu$M.

The photocathode preferably comprises either a magnesium cathode or a cesium-telluride cathode. Alternatively, a thermionic cathode may be utilized.

The radio-frequency electron gun preferably comprises a 5½ cell F band electron gun having an output energy of 15 MeV, for use with a photocathode and a 1.5 cell F band electron gun having an output energy of approximately 15 MeV for use with a thermionic cathode.

The present invention preferably comprises a point-to-point focusing electromagnetic quadrupole triplet for focusing the electrons onto a target.

Thus, according to the present invention, a mobile irradiation device capable of providing energetic electrons and/or short wavelength photons suitable for use in industrial processes and/or the inspection of dense materials is provided. The mobile irradiation device of the present invention may be transported to a remote location wherein such industrial processes and/or inspection are facilitated. Portable electrical power is provided, so as to eliminate the requirement for electrical power at the remote location.

These, as well as other advantages of the present invention will be more apparent from the following description and drawings. It is understood that changes in the specific structure shown and described may be made within the scope of the claims without departing from the spirit of the invention.

DETAILED DESCRIPTION OF THE PREFERRED EMBODIMENTS

The detailed description set forth below in connection with the appended drawings is intended as description of the presently preferred embodiment of the invention and is not intended to represent the only form in which the present invention may be constructed or utilized. The description sets forth the functions and the sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
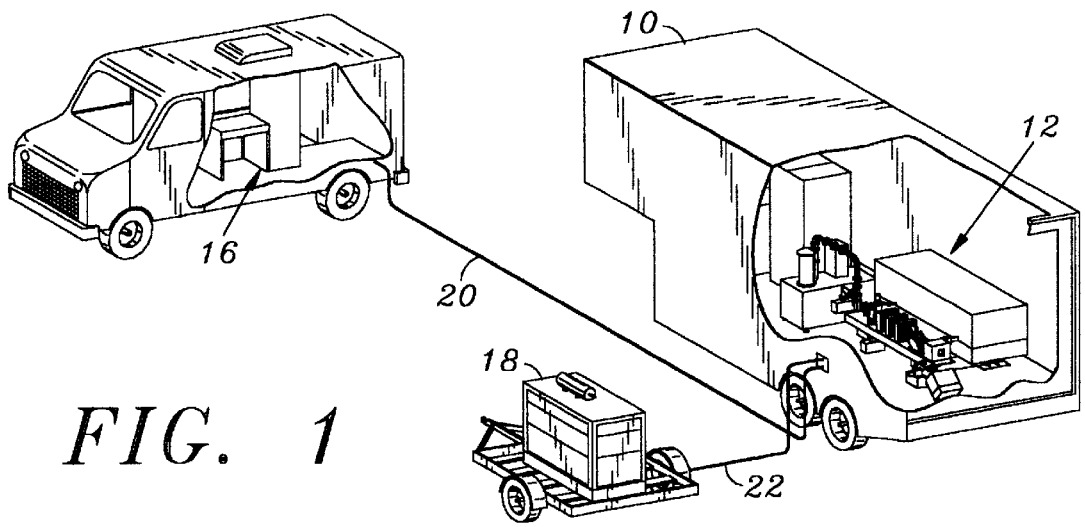
FIG. 1 is a perspective view of the mobile irradiation device of the present invention showing the van containing the control system, the trailer containing the radiation source, and the portable generator for providing power to the van and the trailer.
Figure 2:
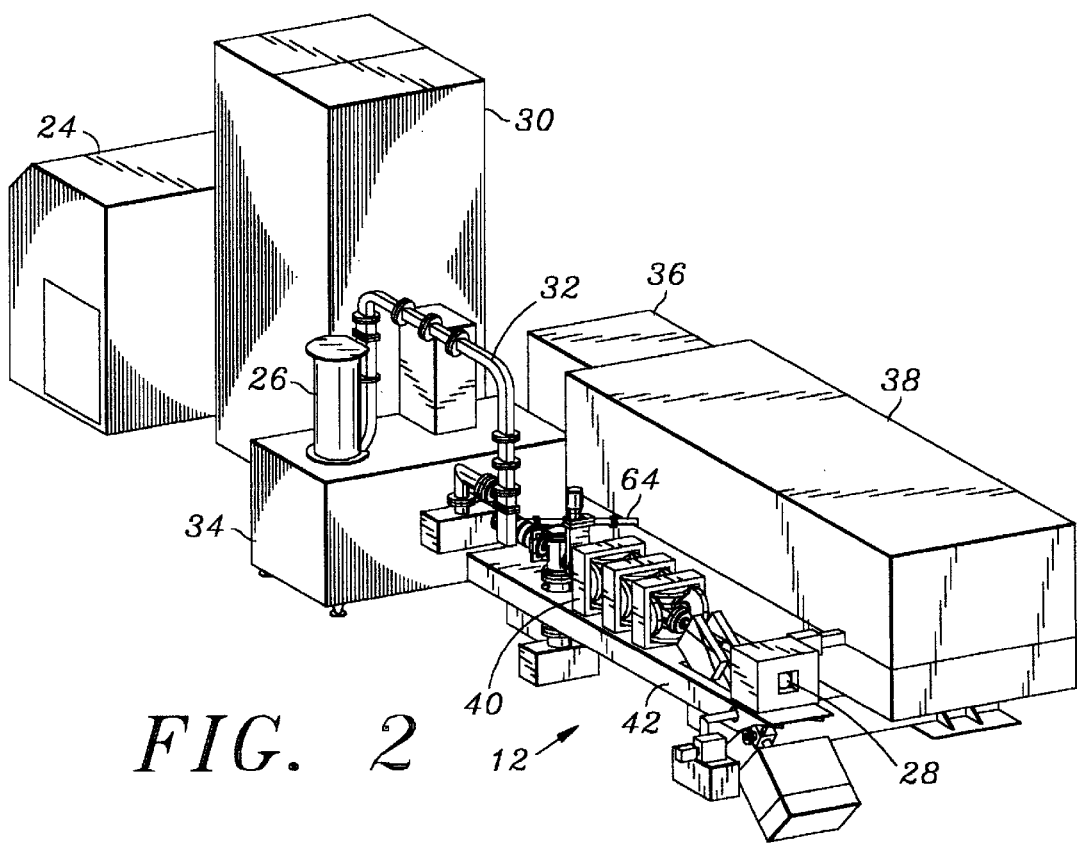
FIG. 2 is a perspective view of the irradiation assembly contained within the trailer.
Figure 3:
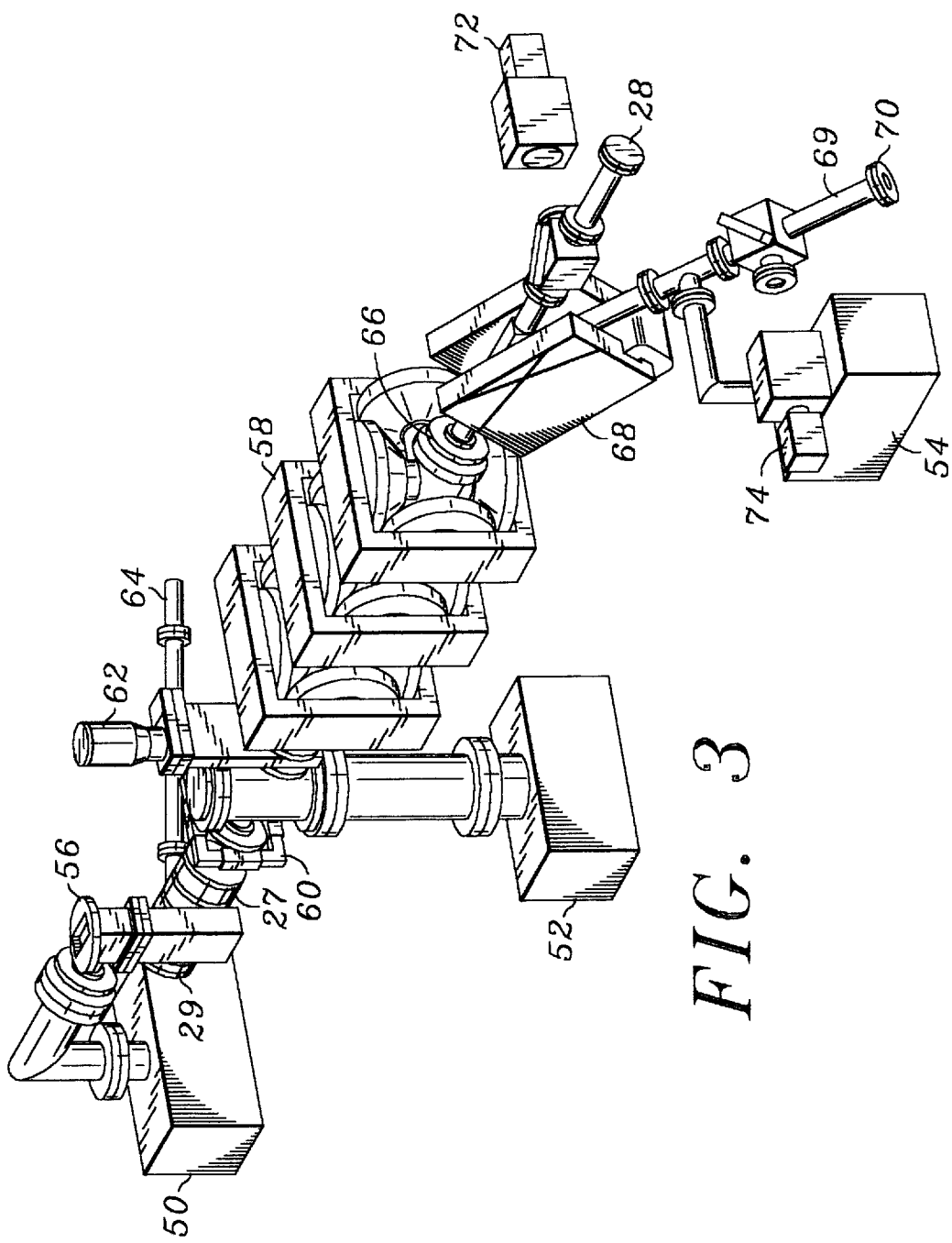
FIG. 3 is a perspective view of the beamline assembly of FIG. 2.
Figure 4:
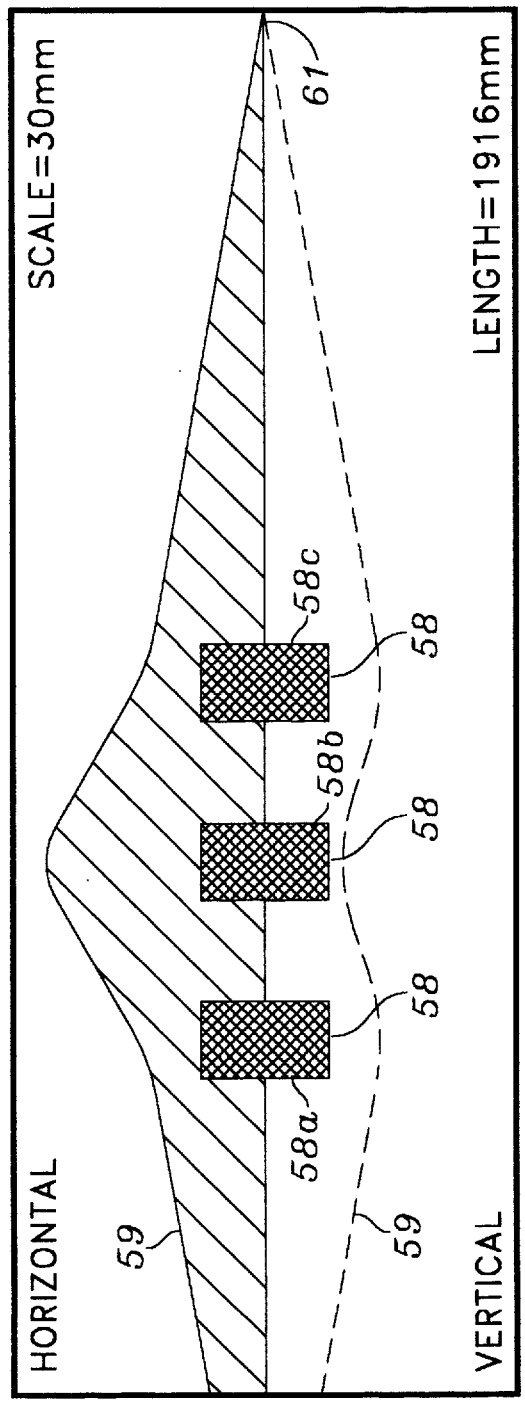
FIG. 4 is a computer generated plot of the horizontal and vertical cross-sectional widths of the electron beam along the length thereof.

The mobile irradiation device of the present invention is illustrated in FIGS. 1–3. FIG. 4 is a computer generated plot of the horizontal and vertical crosssectional widths of the electron beam along the length thereof.

Referring now to FIG. 1, the mobile irradiation device of the present invention generally comprises a trailer 10 containing an irradiation assembly 12, a van 14 containing instrumentation and control electronics 16 and a portable electrical generator 18. Control and instrumentation cables 20 interconnect the instrumentation and control electronics 16 contained within the van 14 and the irradiation assembly 12 contained within the trailer 10. Power cables 22 interconnect the electrical generator 18 and the irradiation assembly 12.

Referring now to FIG. 2, the irradiation assembly 12 comprises cooling water supply 24 for providing cooling water, preferably chilled water to radio frequency Klystron 26 and/or the target 28, as desired.

RF control cabinet 30 houses drive electronics for the RF Klystron 26 and the beamline electronics. RF waveguide 32 guides radio frequency energy from the Klystron 26 to the beamline 40 to facilitate acceleration of the electrons emitted from the photocathode via the laser.

Electrons emitted from the photocathode 29 when the photocathode 29 is struck by the laser beam are thus accelerated by electromagnetic waves generated by the Klystron 26 according to well known principles.

Cooling water from the cooling water supply assembly 24 is utilized to cool the Klystron and the electron gun 27 (FIG. 3).

The RF pulse tank comprises a transformer assembly for driving the RF Klystron 26, so as to generate an electromagnetic wave for accelerating electrons generated by the photocathode 29 of electron gun 27.

The laser power and control assembly 36 drives the laser 38 which provides the laser beam to the photocathode 29 to facilitate the generation of electrons for the electron gun 27.

The beamline 40 comprises focusing elements for shaping and configuring the electron beam as shown in FIG. 4 and discussed in detail below. The beamline and laser support structure 42 provides a dimensionally stable and vibration isolated substrate upon which the beamline 40 and laser 38 are mounted.

Referring now to FIG. 3, the beamline assembly comprises first 50, second 52, and third 54 vacuum pumps for providing vacuum thereto. The first vacuum pump 50 is located proximate the electron gun 27 and primarily provides vacuum to the RF waveguide 56 and the electron gun 27. The second vacuum pump 52 is located intermediate the electron gun 27 and the quadrupole triplet 58 and primarily provides vacuum thereto. The third vacuum pump 54 is located proximate the bending magnet and primarily provides vacuum therefore.

Steering coil 60 aims the electrons emitted by the photocathode 29 along the beamline 40 such that the accelerated electrons pass through the quadrupole triplet 58. The quadrupole triplet comprises three individual quadrupole magnets which shape and/or focus the accelerated electron beam prior to its being incident upon the target 28.

Vacuum valve 62 facilitates repressurization of the beamline after use thereof. Laser tube 64 facilitates the introduction of a laser beam from the laser 38 to the electron gun 27 where the photocathode is located.

Current monitor 66 monitors the intensity of the accelerated electron beam.

Bending magnet 68 diverts the electron beam away from the target 28 to a beam dump 70 when it is desirable to keep the electron beam activated without having it incident upon the target 28.

Camera 72 facilitates visual monitoring of the electron beam prior to its being incident upon the target 28 and camera 74 facilitates visual monitoring of the electron beam prior to its being communicated to the electron dump 70.

Referring now to FIG. 4, a computer generated plot of the horizontal and vertical cross-sectional widths of the electron beam substantially along the width thereof is provided. The three quadrupole magnets 58 are utilized to shape the electron beam 59 so as to maintain a desirable cross-sectional configuration thereof.

The first quadrupole magnet 58a causes the electron beam 59 to converge vertically, but diverge horizontally. The second quadrupole magnet 58 causes the electron beam 59 to converge horizontally, but diverge vertically. The third quadrupole magnet 58c causes the horizontal beam to stop converging at the rate induced by the second quadrupole magnet 58, while causing the electron beam to converge vertically. The net effect of the quadrupole magnets 58 is to cause the electron beam 59 to converge both horizontally and vertically, to a very small cross-sectional area 61, which is suitable for controlled application to a target.

As those skilled in the art will appreciate, radio frequency guns or accelerators are commonly utilized to provide energetic electron beams for a variety of different scientific and industrial applications. However, it will be appreciated that powerful electron sources are commonly extremely heavy and bulky and have high power requirements, so that they are generally not suited for mobile use. This is particularly true when the power requirement therefore exceeds a few kilowatts.

The present invention provides a powerful, yet mobile electron source which may be utilized solely for the energetic electrons provided thereby, or alternatively, may be utilized to facilitate the production of short wavelength photons, i.e., gamma rays and/or x-rays. Thus, the present invention finds particular utility in those instances wherein the item to be irradiated cannot be easily transported to an irradiation facility.

Although it is possible to utilize a thermionic cathode in the present invention, the photocathode is preferred because it is capable of providing a smaller, more concentrated and better controlled electron source.

According to the present invention, electrons from either the photocathode or the thermionic cathode are accelerated to a kinetic energy of approximately 15 MeV via an electron gun, preferably a Klystron actuated RF electron gun. The accelerated electron beam is then focused via the quadrupole triplet 58 beamline 40 and is communicated to either the item to be irradiated (when direct electron irradiation is desired) or to a metal, preferably tantalum intermediate target 28, so as to facilitate the generation of short wavelength photons.

As those skilled in the art will appreciate, the collision of the accelerated electrons with the atoms of the intermediate target 28 produces high energy, short wavelength photons, i.e., gamma rays and/or x-rays, according to the well known Bremstrallhung process. The short wavelength photons generated by the accelerated electrons striking the intermediate target 28 are emitted from the intermediate target 28 mostly in the forward direction, i.e., the direction of the electron beam striking the intermediate target 28. These short wavelength photons are then used to illuminate the ultimate target for purposes of radiography, such as the formation of an x-ray picture. Since the wavelength of the photons emitted by the intermediate target 28 are short, the most energetic of the emitted photons have an energy equal to that of the incident beam electrons, thus making it possible to make radiographic measurements of extremely dense objects.

As those skilled in the art will appreciate, it is desirable to focus the electron beam onto the intermediate target 28 so as to form as small a spot as possible, since the photons emitted from the target 28 in response thereto will thereby be as close of an approximation to a point source as possible. It is desirable to provide photons from as close as possible to a point source so as to provide the highest possible fidelity, thereby enhancing radiographic measurement. Thus, as mentioned above, it is generally more desirable to utilize a photocathode, rather than a thermionic cathode, since smaller spot sizes of the electron beam upon the intermediate target 28 are more easily achieved via the use of such a photocathode. It is well recognized that the generation of energetic electrons via a photocathode is more easily controlled and that the resulting accelerated electron beam therefrom may more readily be focused than from a thermionic cathode. However, it is also well known that a thermionic cathode facilitates the generation of energetic electrons in a more economic manner.

Thus, according to the present invention, the electron beam may be incident directly upon an intermediate target 28, so as to facilitate the generation of short wavelength photons, or, alternatively, may be directly incident upon the ultimate target so as to facilitate electron bombardment for use in such applications as the cross-linking of polymers, the sterilization of bandages, or to effect various different chemical changes.

The power supply is separated from the rest of the system so as to minimize vibration. The use of a separate control vehicle, i.e., the control van 14, enhances safety for the operators of the mobile irradiation device by facilitating operation thereof from a distance therefrom. Alternatively, the instrumentation and control electronics 16 may be located within the trailer 10 along with the irradiation assembly 12. In this instance, radiation shielding may be provided so as to enhance safety for the operator.

The mobile irradiation device of the present invention is capable of continuous, steady-state operation.

The portable electrical generator 18 preferably provides approximately 25 kW, 220 volt, 3 phase electrical output and utilizes a diesel, motor-generator system mounted upon a small, two-wheeled trailer.

The control van 14 preferably comprises a standard cargo van which has been modified to receive the control instrumentation. Preferably, an extra air conditioning unit is provided so as to accommodate the additional heat load of the instrumentation and control electronics.

The trailer 10 preferably comprises as standard, 14,000 pound weight limit, air ride suspension trailer with an enclosed aluminum body having road side access on one side thereof and having full access in the rear thereof. The trailer is equipped with an air conditioning and heating system.

The water cooling system preferably comprises a water tank, an air cooled heat exchanger and a centrifugal pump and operates according to well known principles. The water cooling system provides sufficient cooling to facilitate continuous operation of all of the water cooled systems. The air conditioning and heating system provides for steady operation of the mobile irradiation device at outside temperatures of 32° F. to 90° F.

The RF power supply assembly preferably comprises a 30 MW, 2,856 MHz Klystron pulsed at 10 Hz, a pulse tank, a 30 kV power supply, as well as associated waveguides and RF controls.

The photocathode laser system comprises an optical table, optical elements, a 50 $\mu$F capacitor bank, and associated DC power supply. A 300 mW laser has a wavelength of 1,047 nM, having a pulse width less than 10 picoseconds which can be mode locked and which fires with a frequency of 142.8 MHz. The laser is preferably frequency doubled twice so as to produced 262 $\mu$M radiation upon the magnesium photocathode. Optionally, improved performance is achieved via the use of a cesium-telluride photocathode, although at substantially more expense.

Thus, according to the preferred embodiment of the present invention, the following performance parameters are provided:

| Item | Value | Units |
|---|---|---|
| Energy | 15 | MeV |
| RF Frequency | 2,856 | MHz S-Band |
| Charge per Bunch | 2 | nano-Couloumb |
| RF Repetition Rate | 10 | Hz |
| Bunches per macropulse | 1,400 | |
| Current | 28 | microAmperes Average |
| Power | 420 | Watts Average |
| Radiation | 4,000 | Rad/Min @ 1 Meter est. 60 × 1200 × W^2.63 × I |
| Emittance | <8 | $\pi$ mm-mR RMS Normalized |
| Spot Size | <0.1 | min Diameter RMS |

The electron gun or accelerator preferably comprises a 5½ cell S-Band RF gun having an output energy of approximately 15 MeV. The main beamline consists of this RF electron gun followed by a vacuum port section, a point-to-point focusing electromagnetic quadrupole triplet 58, and a tantalum intermediate target 28.

Vacuum pumping is provided via vacuum pump 52 which is disposed immediately following the electron gun 27 so as to minimize RF breakdown and maximize gun and cathode lifetimes. This is in addition to vacuum pumping at the waveguide 56 via first vacuum pump 50.

The quadrupole triplet 58 is utilized in preference to a solenoid magnet, so as to minimize power requirements and chromatic aberrations. The use of a quadrupole triplet is preferred to that of a quadrupole doublet since it substantially decreases the maximum transverse beam size.

By minimizing the distance from the electron gun 27 to the quadrupole triplet 58, a maximum beam size sufficient to obtain a very small final spot size is obtained.

The beam type preferably has an outer diameter of approximately 2.5 inches (60 mm-ID).

Given a maximum transverse beam 5 ($r_{max}$) within the quadrupole triplet 58, the minimum beam radius ($r_{min}$) at the target is approximately $r_{min} = D \epsilon/r_{max}$, where D is the distance to the target and $\epsilon$ is the local emittance. Substantially, $r_{max}$ is constrained to about 1 cm rms and D to about 1 Meter. The spot radius, $r_{min}$, is 0.05 mm rms. Therefore, it is expected that the local rms emittance must be approximately $\epsilon = r_{min} \, r_{max}/D = 0.5$ mm-mR (15 mm-mR normalized) or smaller, so as to satisfy the target spot radius specification.

The bending magnet 68 preferably comprises a dipole bending magnet such that when switched on the electron beam is diverted into a diagnostic leg 69. The diagnostic leg serves two separate purposes. First, it avoids irradiation of the target while tuning or adjusting the irradiation system. Second, the use of the diagnostic leg 69 functions as a diagnostic tool by coupling of the particle energy to horizontal motion such that it can be used to deduce the average energy and energy spread of the beam.

Alternatively, the diagnostic leg 69 may be eliminated and replaced with moveable radiation shielding about the tantalum intermediate target 28. A small angle bending magnet would then be placed directly over the beamline and used to deflect the on-target spot position. The use of such a small angle bending magnet provides sufficient energy resolution for system maintenance or tune up purposes, while also allowing the pulse quadrupole triplet drift to be substantially shorter, thereby facilitating higher beam emittance. The quadrupole triplet 58 effectively functions as a point-to-point focusing lens.

Although as discussed above, it is possible to utilize a thermionic gun rather than a photocathode, although this would be accomplished at the cost of increased emittance, i.e., beam space volume. Such a thermionic cathode configuration would be substantially the same as the photocathode configuration, although it may optionally utilize a 1½ cell electron gun followed by an alpha magnet and 4 cell RF booster cavity. A comparison of a thermionic gun and a photocathode system is provided below:

| Electron Gun Options | Photocathode | Thermionic Cathode |
|---|---|---|
| Gun (Cells) | 5.5 | 1.5 |
| Alpha Magnet | No | Yes |
| Booster (Cells) | 0 | 4 |
| RF Frequency (MHz) | 2,856 | 2,856 |
| Rep. Rate (Hz) | 10 | 20 |
| Energy (MeV) | 15 | 15 |
| Bunch Charge (nC) | 2 | 0.07 |
| Normalized Emittance (RMS π mm-mR) | <8 | ~16 |
| Pulse Length (μSec) | 10 | 6 |
| Bunch Rep. Rate (MHz) | 142.8 | 2,856 |
| Average Current (μA) | 28.6 | 24 |
| Average Beam Power (Watts) | 429 | 360 |
| Dose (Rad/Min @ 1 Meter) | 4072 | 3393 |
| Modular Input (kW) | 8 | 9.6 |
| RF Other (kW) | 2 | 2 |
| Klystron (kW) | 1 | 1 |
| Beamline (kW) | 1 | 1 |
| Laser (kW) | 2 | 0 |
| Total Power (kW) | 14 | 13.6 |

It is understood that the exemplary mobile irradiation device described herein and shown in the drawings represents only a presently preferred embodiment of the invention. Indeed, various modifications and additions may be made to such embodiment without departing from the spirit and scope of the invention.

Various modifications and additions may be obvious to those skilled in the art and may be implemented to adapt the present invention for use in a variety of different applications.

What is claimed is:

1. A mobile irradiation device for providing at least one of energetic electrons and short wavelength photons, said mobile irradiation device comprising:
   a) a trailer on which is mounted:
      i) a photocathode,
      ii) a laser for illuminating the photocathode,
      iii) a radio-frequency electron gun for accelerating electrons emitted from the laser illuminated photocathode, and
      iv) beamline and spot forming optical elements;
   b) control equipment for controlling items mounted upon the trailer; and
   c) a portable power supply.

2. The mobile irradiation device as recited in claim 1, further comprising a metal target upon which electrons accelerated by the radio-frequency electron gun are incident, so as to effect the production of short wavelength photons.

3. The mobile irradiation device as recited in claim 2, wherein the metal target is configured to produce at least one of gamma rays and x-rays when accelerated electrons are incident thereupon.

4. The mobile irradiation device as recited in claim 1, wherein the radio-frequency electron gun is configured to accelerate electrons emitted from the laser illuminated photocathode to an energy of approximately 15 MeV.

5. The mobile irradiation device as recited in claim 1, further comprising focusing elements for focusing the electrons emitted from the laser illuminated photocathode.

6. The mobile irradiation device as recited in claim 5, wherein the focusing element comprises at least one focusing magnet.

7. The mobile irradiation device as recited in claim 1, wherein the radio-frequency electron gun comprises:
   a) a power supply comprising a 30 MW, 2,856 MHz Klystron pulsed at 10 Hz; and
   b) a pulse tank.

8. The mobile irradiation device as recited in claim 1, wherein the laser comprises a 300 mW laser having a wavelength of 1,047 nM, and a less than 10 picosecond pulse width, and which is configured to be made locked and fired with a frequency of 142.8 MHz.

9. The mobile irradiation device as recited in claim 8, further comprising two frequency doublers for doubling the frequency of a first beam output by the laser twice to produce a second beam having a wavelength of approximately 262 μM.

10. The mobile irradiation device as recited in claim 1, wherein the photocathode comprises at least one of a magnesium cathode and a cesium-telluride cathode.

11. The mobile irradiation device as recited in claim 1, wherein the radio-frequency electron gun comprises a five and one-half cell S-band electron gun having an output energy of 15 MeV.

12. The mobile irradiation device as recited in claim 1, further comprising a point-to-point focusing electromagnetic quadrupole triplet for focusing the electrons onto a target.

13. A mobile irradiation device for providing at least one of energetic electrons and short wavelength photons, said mobile irradiation device comprising:
  a) a trailer upon which is mounted:
    i) a photocathode;
    ii) a laser for illuminating the photocathode; and
    iii) a radio-frequency electron gun for accelerating electrons emitted from the laser illuminated photocathode;
    iv) beamline and spot forming optical elements;
  b) a vehicle containing control equipment for controlling items mounted upon the trailer; and
  c) a portable power supply, configured to be towed.

14. The mobile irradiation device as recited in claim 13, wherein the portable power supply is configured to provide approximately 25 kW at approximately 220 volts, 3 phase.

* * * * *